US00PP10849P

United States Patent [19]

Persson

[11] Patent Number: Plant 10,849

[45] Date of Patent: Apr. 6, 1999

[54] CHRYSANTHEMUM PLANT NAMED 'HONEY CHARM'

[76] Inventor: Kjell-Aake Persson, Köpingegatan 70, 231 000 Trelleborg, Sweden

[21] Appl. No.: 807,691

[22] Filed: Feb. 28, 1997

[51] Int. Cl.[6] ..... A01H 5/00

[52] U.S. Cl. ..... Plt./78

[58] Field of Search ..... Plt./78, 79

[56] References Cited

U.S. PATENT DOCUMENTS

P.P. 6,314 9/1988 VandenBerg ..... Plt./79
P.P. 6,801 5/1989 VandenBerg ..... Plt./79

OTHER PUBLICATIONS

UPOVROM, 1997 Apr., Plant Variety Database, GTI Jouve Retrieval Software, citation for 'Honey Charm'.

*Primary Examiner*—Howard J. Locker
*Attorney, Agent, or Firm*—Foley & Lardner

[57] ABSTRACT

A Chrysanthemum plant named Honey Charm particularly characterized by its flat capitulum form; decorative capitulum type; yellow-orange ray floret color; diameter across face of capitulum of 101 to 121 mm when fully opened, when grown as a pinched disbudded pot mum; photoperiodic flowering response to short days of 53 to 59 days; plant height, with 14 to 16 long days after sticking unrooted cuttings and with 1 to 2 applications of 2500 ppm B-9 SP, ranges from 23 to 28 cm when grown as a pinched pot mum with 4 cuttings in a 15 cm pot; branching pattern is spreading, each plant developing 4 to 5 laterals after pinch; and recommended as a disbud pot mum.

1 Drawing Sheet

The present invention comprises a new and distinct cultivar of Chrysanthemum, botanically known as *Dendranthema grandiflora,* and referred to by the cultivar name Honey Charm.

Honey Charm, identified as 6903 (94-#02100) is a spontaneous mutation of the cultivar Dark Bronze Charm, disclosed in U.S. Plant Pat. No. 6,801, and was selected to expand the color range of the parental variety.

Honey Charm was discovered and selected by inventor Kjell-Aake Persson as one flowering plant within a flowering block of Dark Bronze Charm in March 1994 in a controlled environment in Trelleborg, Sweden.

The first act of asexual reproduction of Honey Charm was accomplished when vegetative cuttings were taken from the initial selection in May 1994 in a controlled environment in Trelleborg, Sweden, by Kjell-Aake Persson.

Horticultural examination of controlled flowerings of successive plantings has shown that the unique combination of characteristics as herein disclosed for Honey Charm are firmly fixed and are retained through successive generations of asexual reproduction.

Honey Charm has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Honey Charm, which, in combination, distinguish this Chrysanthemum as a new and distinct cultivar:

1. Flat capitulum form.
2. Decorative capitulum type.
3. Yellow-orange ray floret color.
4. Diameter across face of capitulum of 101 to 121 mm when fully opened, when grown as a pinched disbudded pot mum.
5. Photoperiodic flowering response to short days of 53 to 59 days.

6. Plant height, with 14 to 16 long days after sticking unrooted cuttings and with 1 to 2 applications of 2500 ppm B-9 SP, ranges from 23 to 28 cm when grown as a pinched pot mum with 4 cuttings in a 15 cm pot.
7. Branching pattern is spreading, each plant developing 4 to 5 laterals after pinch.
8. Recommended as a disbud pot mum.

The accompanying photographic drawing is a side view of a potted mum of Honey Charm, with 4 cuttings in a 15 cm pot, with the colors being as nearly true as possible with illustrations of this type.

Of the commercial cultivars known to the inventor, the most similar in comparison to Honey Charm is the parent cultivar Dark Bronze Charm. All traits of Honey Charm are similar to those of Dark Bronze Charm, except for the ray floret color. The ray floret color of Honey Charm is yellow-orange (closest to R.H.S. 22B), while the ray floret color of Dark Bronze Charm is described as orange-bronze (R.H.S. 167B to 168C).

In the following description color references are made to The Royal Horticultural Society Colour Chart. The color values were determined on plant material grown as a pinched disbudded pot mum in Salinas, Calif. on Aug. 30, 1996.

Classification:

*Botanical.*—*Dendranthema grandiflora* cv Honey Charm.

*Commercial.*—Flat decorative disbud pot mum.

Inflorescence

A. Capitulum:

*Form.*—Flat.

*Type.*—Decorative.

*Diameter across face.*—101 to 121 mm when fully opened.

B. Corolla of Ray Florets:

*Color* (*general tonality from a distance of three meters*).—Yellow-orange.

*Color* (*upper surface*).—Closest to 22B.

*Color* (*under surface*).—Closest to 22D.
*Shape.*—Flat, straight, slightly ribbed.

C. Corolla of Disc Florets:
*Color* (*mature*).—154B to 154C.
*Color* (*immature*).—149B.

D. Reproductive Organs:
*Androecium.*—Present on disc florets only, very few; scant pollen.
*Gynoecium.*—Present on both ray and disc florets.

Plant

A. General Apperance:
*Height.*—23 to 28 cm when grown as a pinched pot mum with 14 to 16 long days after sticking unrooted cuttings prior to start of short days, with 1 to 2 applications of 2500 ppm B-9 SP.
*Branching pattern.*—Spreading, each plant developing 4 to 5 laterals after pinch.

B. Foliage:
*Color* (*upper surface*).—147A.
*Color* (*under surface*).—147B.
*Shape.*—Lobed and serrated.

What is claimed is:

1. A new and distinct Chrysanthemum plant named Honey Charm, as described and illustrated.

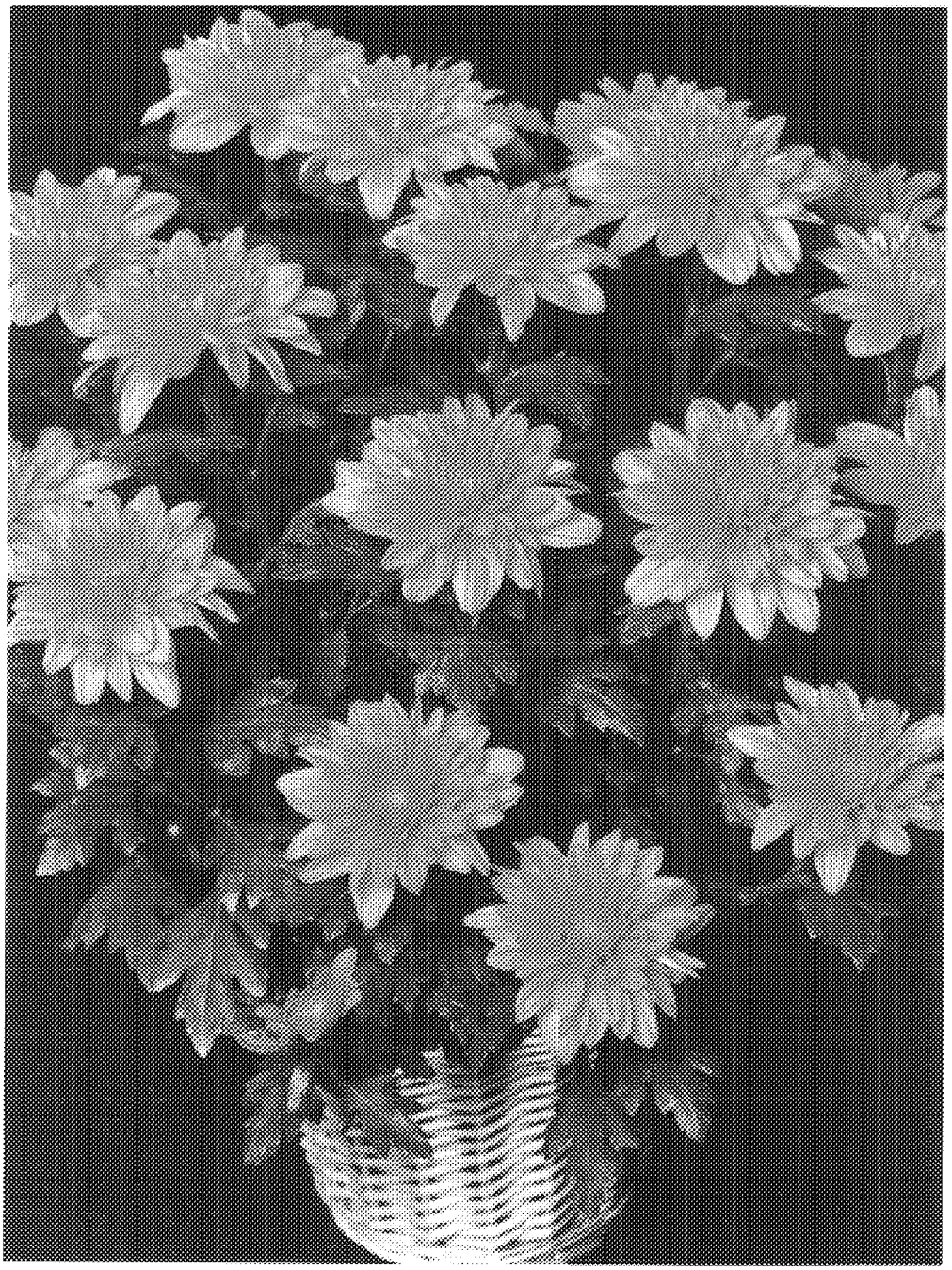

* * * * *